(12) United States Patent
Li et al.

(10) Patent No.: US 11,092,584 B2
(45) Date of Patent: Aug. 17, 2021

(54) COMPOSITE LED MODULE AND WATER QUALITY MONITORING DEVICE USING THE SAME

(71) Applicant: Nanjing University, Nanjing (CN)

(72) Inventors: Wentao Li, Nanjing (CN); Yaping Wu, Nanjing (CN); Aimin Li, Nanjing (CN); Guangyan Zhang, Nanjing (CN); Yan Li, Nanjing (CN); Jianjun Zhuang, Nanjing (CN); Wenxiang Ji, Nanjing (CN); Haonan Jiang, Nanjing (CN); Chunming Chen, Nanjing (CN); Yuze Han, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 16/729,486

(22) Filed: Dec. 30, 2019

(65) Prior Publication Data

US 2020/0209208 A1 Jul. 2, 2020

(51) Int. Cl.
*G01N 33/18* (2006.01)
*G01N 21/47* (2006.01)
*G01N 21/59* (2006.01)
*G01N 21/64* (2006.01)
*H01L 25/075* (2006.01)
*H01L 25/16* (2006.01)

(52) U.S. Cl.
CPC ............ *G01N 33/18* (2013.01); *G01N 21/47* (2013.01); *G01N 21/59* (2013.01); *G01N 21/64* (2013.01); *H01L 25/0753* (2013.01); *H01L 25/167* (2013.01)

(58) Field of Classification Search
CPC ........ G01N 21/47; G01N 21/59; G01N 21/64; G01N 33/18; G01N 2021/3155; G01N 2021/3181; G01N 21/255; G01N 21/31; G01N 21/33; G01N 21/532; G01N 21/645; G01N 21/6486; G01N 2201/0627; H01L 25/0753; H01L 25/167; G01D 21/02
USPC ................................. 356/432–448, 213–236
See application file for complete search history.

(56) References Cited

U.S. PATENT DOCUMENTS

| | | | |
|---|---|---|---|
| 10,570,028 B2 * | 2/2020 | Liao | C02F 1/725 |
| 2019/0032864 A1 * | 1/2019 | Xiong | F21V 23/023 |
| 2020/0312226 A1 * | 10/2020 | Hussell | G09G 3/342 |

* cited by examiner

*Primary Examiner* — Tri T Ton
(74) *Attorney, Agent, or Firm* — Duane Morris LLP

(57) ABSTRACT

Disclosed is a composite LED module comprising a 230±10 nm deep-ultraviolet light LED, a 275±10 nm deep-ultraviolet light LED, and 0 to 3 visible light LED(s), packed in a same substrate. Also disclosed are a water quality monitoring device and a water quality monitoring probe containing the composite LED module.

15 Claims, 8 Drawing Sheets

COMPOSITE LED MODULE AND WATER QUALITY MONITORING DEVICE USING THE SAME

TECHNICAL FIELD

The present disclosure is directed to environmental protection and online water quality monitoring. Particularly, the present disclosure discloses a composite LED module, and a multi-parameter water quality monitoring device based on the composite LED module.

BACKGROUND

Online water quality monitoring is a process for assessment of water quality by online determining the pollutant types, the concentration of each pollutant and the pollution trends in water. It is an important method to prevent water pollution and ensure drinking water safety, and is also helpful to wastewater treatment, river and lake water management and drinking water purification. Multiple parameters have been used for online water quality monitoring, including physical indices, chemical indices, and biological indices.

Dissolved organic matter (DOM) is widely present in natural water and polluted water systems, including high molecular weight proteins, middle molecular weight humic acids and fulvic acids, and low molecular weight substances. DOM is a predominant component that contributes to chemical oxygen demand (COD) in wastewater, and is the main cause of black smelly water. Also, chlorination of drinking water for disinfection may generate carcinogenic byproducts from reactions between DOM and chlorine. DOM serves as carbon source to support the growth of microorganisms in the water pipes, leading to biological contamination in water distribution system. The methods for measuring DOM concentration include chemical methods and spectroscopic methods. The chemical methods mainly include the chemical oxygen demand determination and the total organic carbon measurement, and the spectroscopic methods mainly include UV-Vis spectroscopy and fluorescence spectroscopy. The chemical methods are widely used, but the online monitoring devices using such chemical methods are usually large, expensive and complex in structure, and require a long time to complete the analysis. Further, such chemical methods use chemical reagents, which generate chemical products and make secondary contamination, and cost a lot for device maintenance and treatment of the generated chemical products. On the other hand, the spectroscopic methods are quick and sensitive in DOM analysis, and use no chemical agents. The ultraviolet spectroscopy may be used to test the aromatic compounds containing one or more benzene rings, and is thus applicable to the proteins, humic acids, fulvic acids, and some small compounds containing one or more benzene rings. The fluorescent DOM includes proteins, humic substances and pigments such as chlorophyll. The proteins and humic substances emit fluorescence at a wavelength of 310-360 nm and 400-500 nm, respectively, and the chlorophyll has an emission peak at about 685 nm. The 310-360 nm fluorescence signals may be used to determine the substances in water containing a phenol-like or aniline-like structure, including proteins, humic substances, fulvic acids, tryptophan, tyrosine, and some small molecules, and the 400-500 nm fluorescence may be used to determine humic acids, fulvic acids and aromatic compounds containing fused rings such as naphthol, naphthyl amine, quinine, and pterin (peak emission at about 450 nm). The ultraviolet absorbance (UV254), the 310-360 nm fluorescence and the 400-500 nm fluorescence can be used to indicate the type and the concentration of DOM in water to some extent.

Turbidity is a measurement of the degree to which a solution reduces light penetration due to light scattering and absorption caused by suspended matters. Turbidity can reflect the content of suspended solids and colloids such as soil, gravel, and plankton in water, and it is one of the water quality indicators that can be directly observed and felt by people. The turbidity, together with the pH, temperature, dissolved oxygen, and electrical conductivity, are the most commonly used parameters in water quality monitoring. The turbidity can be measured by light absorption or scattering related methods, wherein the light scattering related method is a technique that has been widely for online water quality monitoring.

Due to wastewater discharge and extensive use of chemical fertilizers, eutrophication is particularly common now and mostly arise from the overloads of nutrients containing, for instance, nitrogen and phosphorus. Nitrates are the final products from oxidative degradation of nitrogen-containing organic matters, and nitrate nitrogen ($NO_3$—N) is the most common form of nitrogen present in the natural waterbody. The nitrate nitrogen can be measured by phenoldisulfonic acid related method, ultraviolet spectroscopy, and ion chromatography. The online monitoring device using the phenoldisulfonic acid related method is commercially available, but phenoldisulfonic acid is not stable and its solution needs to be prepared from time to time, which limits the use of this device. In the ultraviolet spectroscopy, nitrate absorbs light at 220 nm, while the UV absorbance of DOM at 220 nm ($A_{220}$) is almost two times as much as that at 275 nm ($A_{275}$). The absorbance of nitrate can be determined as $A_{220}-2*A_{275}$, where the influence of DOM is reduced or eliminated.

In sum, the online monitoring of DOM, turbidity and nitrate nitrogen may be done by spectroscopy.

S:CAN, an Austrian company, developed a submersible UV-Vis spectrometer probe, which uses a pulse xenon lamp as the light source and measures absorbance at 190-720 nm. The probe determines the concentration of nitrate and DOM using the absorbance at wavelengths shorter than 240 nm and 250-370 nm, respectively, and the absorbance at 380-750 nm is used to determine, for instance, the turbidity and color. However, the xenon lamp in the submersible UV-Vis spectrometer probe emits light spanning a certain range of wavelengths, and a complex light splitter is therefore needed. Further, the probe needs a complex power supply system to provide a pulse voltage of 500 V or higher, and also an expensive spectral detector to work together, making it hard to manufacture a miniaturized spectrometer. Along with the development of the smart water monitoring platform, there is an urgent need for a small, cheap, energy-efficient and low-maintenance water quality sensor or monitoring device, with which water in more sites can be monitored. And the online monitoring of DOM concentration using spectroscopy has been eventually accepted and widely used in water quality monitoring programs.

Light emitting diode (LED) is small, cheap and energy-efficient, and emits a light beam of a narrow spectrum with a high switching rate and a low operating voltage. While the pulse xenon lamp is favored in that it may emit ultraviolet lights with wavelengths shorter than 240 nm for online analysis of nitrate nitrogen. Recently, the AlGaN based LED has been developed to emit light having a wavelength as short as 210 nm but with a low emission efficiency, while a GaN based LED was prepared in US in 2017 to stably emit 232 nm light with much improved emission efficiency. The US patent application US20170254752A1 discloses a water monitoring probe which uses a 229 nm light-emitting LED as the light source and measures nitrate concentration in water using UV absorbance at 229 nm. However, there are a large quantity of DOM in natural water, which has extensive absorption at 229 nm and thus disturbs the nitrate measurement. The Chinese invention patent application CN201410502662.9 discloses a UV-fluorescence dual-signal water quality monitoring device using a LED as the light source, as well as a method of using that device. The Chinese invention patent application CN201510738667.6 discloses a UV-fluorescence triple-signal water quality monitoring sensor using a single UV-LED as the light source, as well as the use of the sensor. These two applications both adopt a single UV-LED as the light source to measure the UV absorbance and the fluorescence signals from proteins or humic substances so as to monitor DOM concentration in water.

The devices mentioned above are applicable to monitoring DOM in water of low turbidity such as drinking water and reclaimed wastewater. If they are used to online monitor the water quality in the field, there might be several issues. (1) The turbidity level of water interferes with the determination of DOM, and DOM concentration should be corrected based on the turbidity. (2) The nitrate or nitrate nitrogen level is one of the most important parameters in current online water quality monitoring, but cannot be determined using the water quality monitoring devices described in the above-mentioned Chinese patent applications. (3) Water color cannot be determined by these water quality monitoring devices. (4) The LED light intensity attenuates over time, decreasing the spectral signal accuracy.

SUMMARY OF THE INVENTION

The present disclosure aims to provide a composite LED module and a water quality monitoring device using the composite LED module.

The present disclosure discloses a composite LED module comprising a 230±10 nm deep-ultraviolet-light LED, a 275±10 nm deep-ultraviolet-light LED, and zero to three visible-light LED(s), packaged on a same substrate or circuit board, wherein these LEDs use a common anode and independent cathodes, a common cathode and independent anodes, or independent cathodes and anodes, and the pins are connected to corresponding driving circuits in such a way that each LED can be switched on/off independently.

The visible-light LED may be selected from the group consisting of a 465±10 nm blue light LED, a 520±10 nm green light LED, and a 655±10 nm red light LED. The composite LED module may emit a combination of (1) 230±10 nm deep-ultraviolet light and 275±10 nm deep-ultraviolet light, (2) 230±10 nm deep-ultraviolet light, 275±10 nm deep-ultraviolet light and 465±10 nm blue light, (3) 230±10 nm deep-ultraviolet light, 275±10 nm deep-ultraviolet light and 520±10 nm green light, (4) 230±10 nm deep-ultraviolet light, 275±10 nm deep-ultraviolet light and 655±10 nm red light, or (5) 230±10 nm deep-ultraviolet light, 275±10 nm deep-ultraviolet light, 465±10 nm blue light, 520±10 nm green light and 655±10 nm red light.

In another respect, the present disclosure provides a multi-parameter water quality monitoring device based on the composite LED module described above, which may further comprises an ultraviolet-visible light-detecting photodiode B, a fluorescence-detecting photodiode C, a quartz plate A, a quartz plate B, a quartz plate C and a band-pass filter.

The quartz plate A, the quartz plate B and the quartz plate C form a U-shaped groove I in which a water sample to test may flow. The quartz plate A and the quartz plate B are arranged opposite to each other, forming the vertical side walls of the U-shaped groove I. The quartz plate C is horizontally arranged at the bottom of the U-shaped groove I, which are perpendicular to the quartz plates A and B.

The LEDs packaged in the composite LED module emit ultraviolet and/or visible light of different wavelengths in an alternating pattern (in turns), and the light transmits through the quartz plate A to the water sample in the U-shaped groove I where light absorption, light scattering and fluorescence emission occur. The emitted fluorescence transmits through the quartz plate C and the band-pass filter, and is detected by the fluorescence-detecting photodiode C. Meanwhile, the blue light is scattered by particulates and/or colloids and passes through the band-pass filter for humic-based fluorescence detection and detected by the fluorescence-detecting photodiode C. The light that has not been absorbed and scattered goes through the water sample and then the quartz plate B, and reaches the ultraviolet-visible light-detecting photodiode B.

Further, the multi-parameter water quality monitoring device of the present disclosure may further comprise a beam splitter and a reference light-detecting photodiode A, wherein the beam splitter is arranged at a 45° angle relative to the central axis of the composite LED module. The beam splitter splits a beam of light from the composite LED module into two, one beam transmitting in the original direction and used for measurement, and the other transmitting in a direction perpendicular to the original direction and used as a reference. The optical power ratio of the light beam transmitting in the original direction to the other light beam ranges from 10/90 to 90/10.

The central axis of the composite LED module may be arranged perpendicular to or in parallel to the central axis of the U-shaped groove.

When the central axis of the composite LED module is perpendicular to that of the U-shaped groove, the central axis of the reference light-detecting photodiode A is arranged perpendicular to that of the composite LED module.

When the central axis of the composite LED module is in parallel to that of the U-shaped groove, the central axis of the reference light-detecting photodiode A is arranged in parallel to that of the composite LED module.

The multi-parameter water quality monitoring device of the present disclosure may further comprise a reflector disposed with a 45° angle relative to the central axis of the ultraviolet-visible light-detecting photodiode B. The light that are not absorbed and scattered by water samples in U-shaped groove goes through the quartz plate B, and then reflected by the reflector to the ultraviolet-visible light-detecting photodiode B.

The reference light-detecting photodiode A and the ultraviolet-visible light-detecting photodiode B may be UV enhanced silicon photodiodes or composite photodiodes each packaged with an AlGaN based deep-ultraviolet light detecting chip and a silicon photovoltaic plate.

The silicon photovoltaic plate in the composite photodiode mainly senses the ultraviolet-visible light having a wavelength of 250 nm or longer to analyze DOM, turbidity and water color, while the AlGaN based deep-ultraviolet light-detecting chip mainly detects the 230±10 nm ultraviolet light to measure nitrate nitrogen. The composite photodiode packaged with the AlGaN based deep-ultraviolet light-detecting chip and the silicon photovoltaic plate may be specifically designed in such a way that the silicon photovoltaic plate is 凹-shaped and the AlGaN based deep-ultraviolet light-detecting chip is in the groove part of the 凹-shaped silicon photovoltaic plate.

A TO-8 or TO-46 package may be used to pack the ultraviolet-visible light detecting photodiode B, and the reference light detecting photodiode A may use the surface mount package or TO-8 or TO-46 package.

The ultraviolet absorbance based measurement may comprise the determination of absorbance at 230±10 nm ($A_{230±10}$), and the determination of absorbance at 275±10 nm ($A_{275±10}$), wherein nitrate has predominant absorbance at 230±10 nm, and DOM has absorbance at both 230±10 nm and 275±10 nm. The absorbance of DOM at 230±10 nm ($α×A_{275±10}$) may be calculated by multiplying $A_{275±10}$ by a coefficient α, and the nitrate level can be determined as $A_{230±10} - α×A_{275±10}$ such that the influence from DOM absorbance is reduce or even eliminated.

The measurement of visible light absorbance comprises the determination of the absorbance at 465±10 nm (blue light), absorbance at 520±10 nm (green light), absorbance at 655±10 nm (red light), and the combinations. The absorbance of individual visible light may be used to determine the turbidity. The absorbance of three visible light (blue, green and red) may be combined to determine the turbidity, and may be also used to determine the water color based on three primary color principle and Newton color wheel.

The band-pass filter may be (a) a band-pass filter covering 320-360 nm for detection of protein-based fluorescence, (b) a band-pass filter covering 380-500 nm for detection of humic-based fluorescence, or (c) a band-pass filter covering 320-500 nm for detection of the total fluorescence from both proteins and humic substances.

The present disclosure also provides a monitoring probe based on the multi-parameter water quality monitoring device described above, comprising a casing, an optical detection unit and an electronic circuit unit.

The casing comprises a U-shaped front cover, a cylinder and a back cover. The U-shaped front cover is waterproof and allows light transmission, and functions to receive and fix the optical detection unit. The U-shaped front cover has a cylindrical main body, and a U-shaped groove II is disposed at the top or side surface of the main body. Two lateral sides and the bottom part of the U-shaped groove II are further provided with holes and a groove at the center part of the bottom side, respectively, and bonded with the quartz plate A, quartz plate B and quartz plate C, respectively.

The back cover is open in the middle where a power cable is fixed with a connector in an air-tight and water-tight manner.

The cylinder mainly functions to receive the electronic circuit unit, and the back cover mainly fixes the cable in a water-tight way.

The electronic circuit unit comprises a microcontroller, a power supply module, signal amplification circuits, an analog-to-digital converter, a communication module, and a temperature sensor. The power supply module supplies power to various components in the electronic circuit unit. The microcontroller outputs digital signals to driving circuits to control the on/off of the LEDs emitting lights of different wavelengths in the composite LED module in a time division multiplexing way, wherein the deep-ultraviolet light is absorbed by DOM in the water, and the proteins and humic substances in DOM emit fluorescence, and the blue light, if applicable, transmits to the particulates in the water sample where light scattering occurs. The light at different wavelengths attenuates due to light absorption and scattering when transmitting through the water sample, and the absorbance can be calculated based on this. Three signal amplification circuits are used to process the electronic signals generated by the photodiode A, photodiode B and photodiode C, respectively, wherein the three photodiodes are in the photovoltaic mode. Preferably, the circuits are designed as lock-in amplifiers. The amplified signals are converted to digital signals in the analog-to-digital converter which are collected by the microcontroller, and the microcontroller and the master computer use the MODBUS-RTU protocol for communication.

The composite LED module and the device using the same of the present disclosure have the following advantages over the prior art.

(1) The present disclosure provides a composite LED module, wherein LEDs with different light wavelengths are packed in a same substrate or circuit board. The LEDs are turned on/off in a time division multiplexing way, as required in water quality analysis. As compared to the conventional xenon lamp based light source and system, the LED module of the present disclosure is small in size, low in power consumption and provides a light beam of a certain spectral color.

(2) Taking advantage of the high switching rate of the LED, the multi-parameter water quality monitoring probe with the composite LED module of the present disclosure may have the LEDs emit light waves at preset frequencies and demodulate the LED light or fluorescence from relatively intensive interfering environmental lights using the lock-in amplification method.

(3) The multi-parameter water quality monitoring probe with the composite LED module of the present disclosure may use UV-Vis spectroscopy, fluorescence spectroscopy and light scattering to determine the DOM and nitrate concentration, turbidity and water color simultaneously.

(4) The multi-parameter water quality monitoring probe with the composite LED module of the present disclosure may use a beam splitter to spilt the LED light into a light beam for water quality measurement and a light beam for reference, so that the intensity fluctuation of the light emitted from the deep-ultraviolet LEDs can be monitored and corrected according to the reference light intensity.

(5) The multi-parameter water quality monitoring probe with the composite LED module of the present disclosure measures both the ultraviolet light absorbance at 230±10 nm and the ultraviolet light absorbance at 275±10 nm to more precisely determine the nitrate concentration in natural water sample, because the influences from DOM absorbance can be reduced or even eliminated.

The present disclosure will be described in more details with reference to the drawings.

REFERENCE SIGNS

1—U-shaped front cover, 2—cylinder, 3—back cover, 4—power cable, 5—quartz plate A, 6—quartz plate B, 7—quartz plate C, 8—circuit board, 9—composite LED module, 10—light beam splitter, 11—reference light-detecting photodiode A, 12—ultraviolet-visible light-detecting photodiode B, 13—fluorescence-detecting photodiode C, 14—band-pass filter, 15—reflector, 121—AlGaN based deep-ultraviolet light-detecting chip, 122—silicon photovoltaic plate.

DETAILED DESCRIPTION OF THE INVENTION

The present disclosure will be further described with reference to the drawings and examples.

Example 1

In the present example, a composite LED module based multi-parameter water quality monitoring probe is provided, comprising a casing, an optical detection unit and an electronic circuit unit, which may measure DOM concentration, nitrate concentration, turbidity, and water color.

Figure 1:
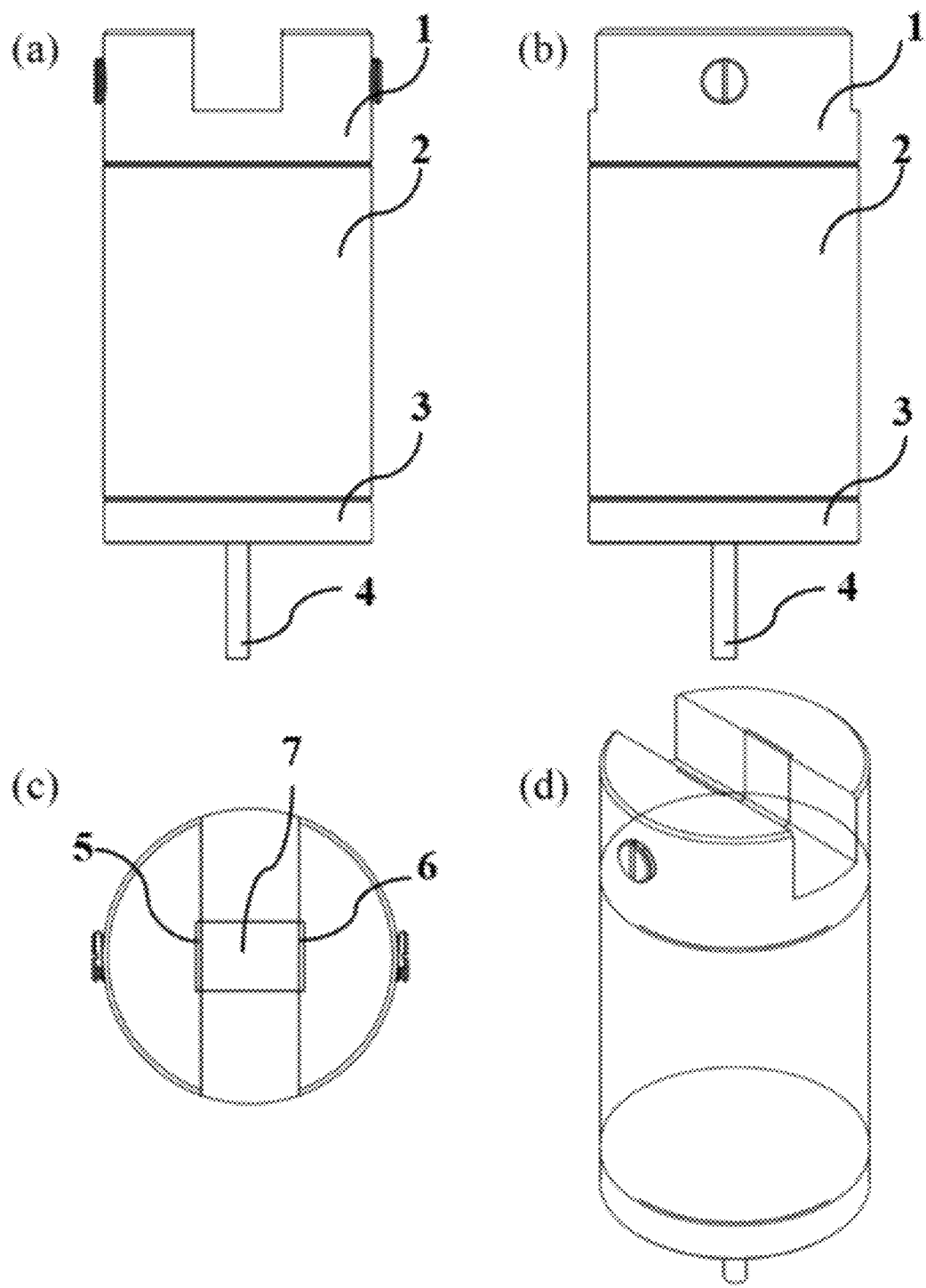
FIG. 1 is a schematic diagram showing the appearance of a multi-parameter water quality monitoring probe using a composite LED module according to an embodiment, including a front view (a), a side view (b), a top view (c) and an axonometric view (d).

As shown in FIG. 1, the casing comprises a U-shaped front cover 1, a cylinder 2 and a back cover 3. The main body of the U-shaped front cover 1 is a cylinder, with a U-shaped groove on the top surface. The two lateral sides and the bottom part of the U-shaped groove are further provided with holes and a groove, and bonded with the JGS1 quartz plate A 5, quartz plate B 6 and quartz plate C 7, respectively, such that the U-shaped groove is waterproof and allows light transmission, making it suitable for optical measurement. The cylinder 2 is designed to receive a circuit board 8 of the electronic circuit unit. The back cover 3 has a hole at the center where a power cable 4 is fixed with an air-tight and water-tight connector. That is, the back cover 3 mainly function to fix the power cable 4 in an air-tight and water-tight manner.

Figure 2:
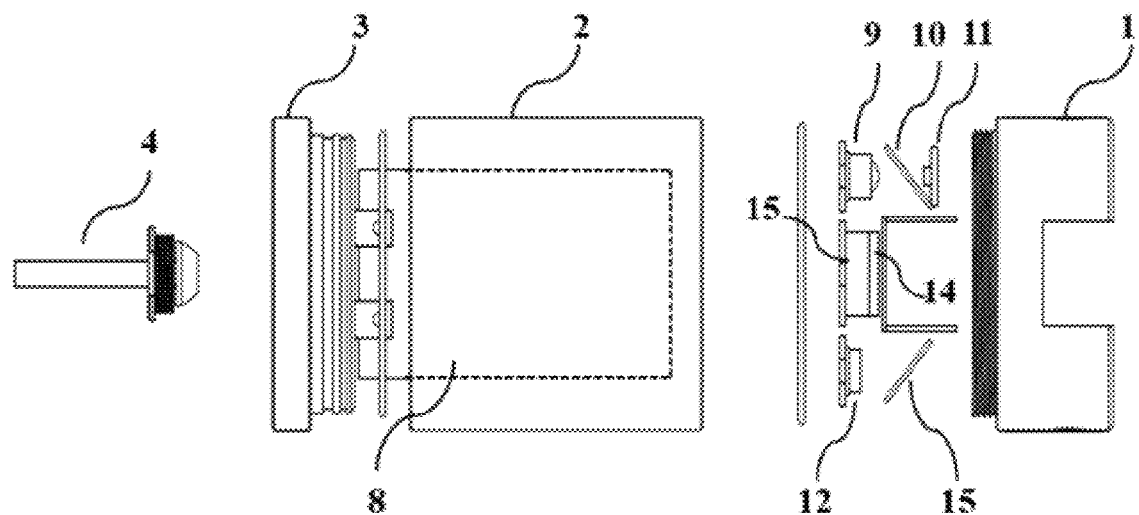
FIG. 2 is a schematic diagram showing the internal structure of the multi-parameter water quality monitoring probe using a composite LED module.
Figure 3:
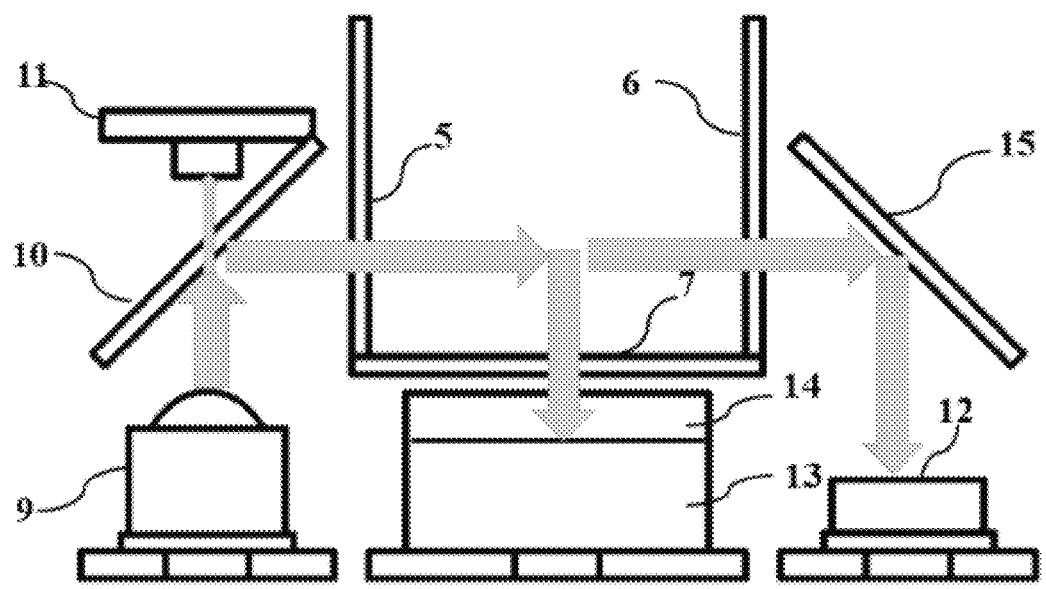
FIG. 3 is a schematic diagram showing an optical detection unit of the multi-parameter water quality monitoring probe using a composite LED module.

As shown in FIG. 2 and FIG. 3, the optical detection unit comprises a composite LED module 9, a beam splitter 10, a reference light-detecting photodiode A 11, an ultraviolet-visible light-detecting photodiode B 12, a fluorescence-detecting photodiode C 13, the quartz plate A 5, the quartz plate B 6, the quartz plate C 7, a band-pass filter 14 and a reflector 15.

The composite LED module 9 comprises a 230±10 nm deep-ultraviolet light LED, a 275±10 nm deep-ultraviolet light LED, a 465±10 nm blue light LED, a 520±10 nm green light LED and a 655±10 nm red light LED, packaged on the same substrate, wherein these LEDs use a common anode and independent cathodes, or a common cathode and independent anodes, and the pins are connected to corresponding driving circuits in such a way that the independent control of each LED chip is enabled. A quartz lens is arranged above the LEDs to concentrate light rays so that the LED module has a beam angle of about 7°.

The beam splitter 10 is arranged at a 45° angle relative to the central axis of the composite LED module 9, to split the light beam from the composite LED module 9 into two beams, one transmits in the original direction and the other transmits in a direction perpendicular to the original direction. In this Example, the light beam transmitting through the splitter is used as the reference light, the reflected light beam is used for measurement, and the optical power ratio of the transmitted light beam to the reflected light beam is 10/90.

Figure 4:
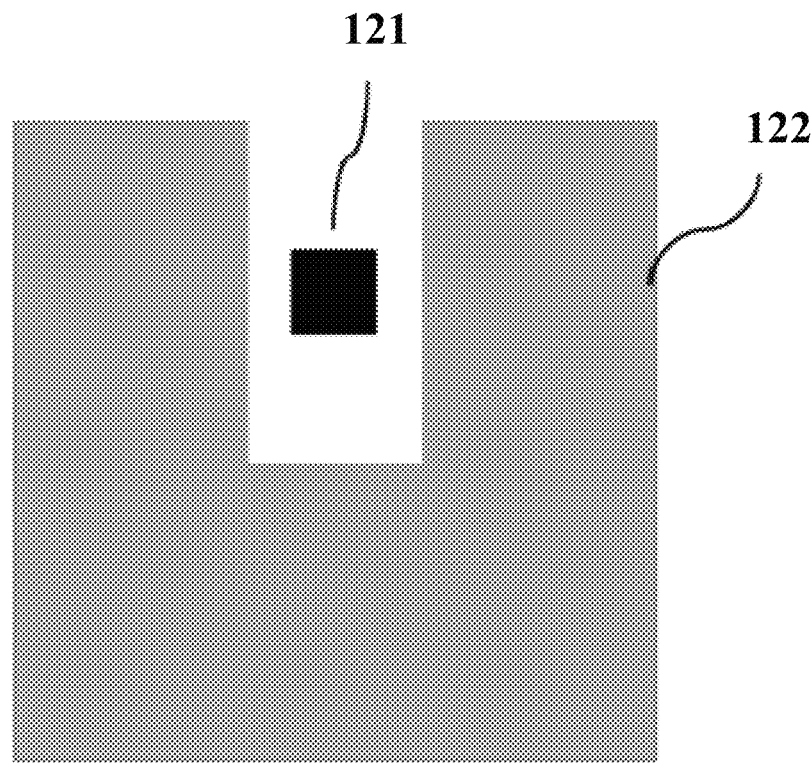
FIG. 4 is a schematic planar view of a composite photodiode in the multi-parameter water quality monitoring probe using a composite LED module.

The reference light-detecting photodiode A 11 and the ultraviolet-visible light-detecting photodiode B 12 are both composite photodiodes each packed with an AlGaN based deep-ultraviolet light-detecting chip 121 and a silicon photovoltaic plate 122. The composite photodiode is shown in FIG. 4. The AlGaN based deep-ultraviolet light detecting chip 121 is 1×1 mm² in size, and the silicon photovoltaic plate 122 is shaped as 凹. The AlGaN based deep-ultraviolet light-detecting chip is positioned at the groove part of the 凹-shaped silicon photovoltaic plate. The silicon photovoltaic cell 122 mainly senses the ultraviolet-visible light having a wavelength of 250 nm or longer to analyze DOM, turbidity and water color. The AlGaN based deep-ultraviolet light detecting chip 121 detects the 230±10 nm deep-ultraviolet light to measure nitrate and also detects the 275±10 nm deep-ultraviolet light to measure DOM. The reference light-detecting photodiode A 11 adopts the surface mount package, and a TO-8 package may be used to pack the ultraviolet-visible light-detecting photodiode B 12.

The band-pass filter 14 passes light having a wavelength of 320-500 nm and rejects 99.9% of light with other wavelengths. The fluorescence-detecting photodiode C 13 is a silicon photovoltaic plate with TO-8 package.

Figure 5:
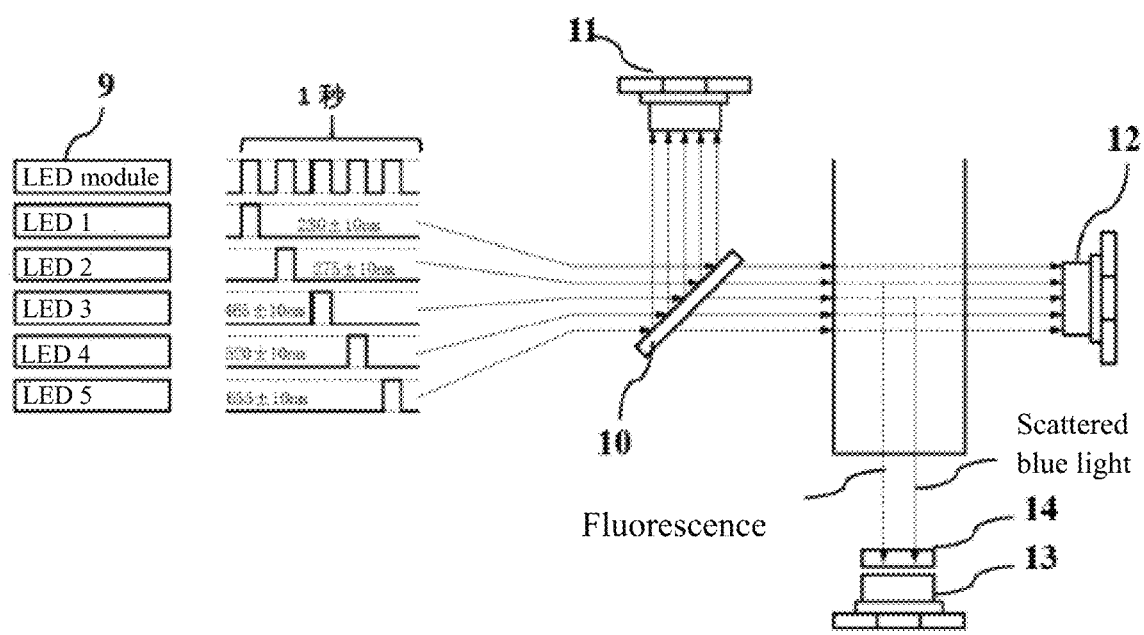
FIG. 5 is a schematic diagram illustrating the time division multiplexing principle adopted by the optical detection unit of the multi-parameter water quality monitoring probe using a composite LED module.

How these optical components work and function can be figured out with reference to FIG. 5. The LEDs packed in the composite LED module 9 are controlled by driving circuits in a time-division multiplexing manner to emit ultraviolet or visible lights of different wavelengths in an alternating pattern, each cycle lasting, e.g., 1 second. That is, every LED is switched on/off at a high switching rate of 1 kHz during its working time (0.1 second). The light beam emitted from the composite LED module 9 is split by the beam splitter 10 into two beams, one reaching the reference light-detecting photodiode A 11, the other transmitting through the quartz plate A 5 and going into the water sample in the U-shaped groove positioned at the outer face of the probe where light absorption, scattering and fluorescence emission occur.

The detection of the generated fluorescence and the scattered light will be described below. When the LED emitting 275±10 nm deep-ultraviolet light works, fluorescence is generated from the proteins and humic substances contained in DOM, which passes through the quartz plate C 7 and the band-pass filter 14 and detected by the photodiode C 13. When the LED chip emitting 465±10 nm blue light works, the blue light is scattered by particulates and colloids, and the scattered blue light transmits through the band-pass filter 14 allowing transmission of 320-550 nm light and detected by the photodiode C 13.

The detection of ultraviolet-visible light absorbance is described below. The light that has not been absorbed or scattered transmits through the water sample, the quartz plate B 6 and reflected by the reflector 15 to the ultraviolet-visible light-detecting photodiode B 12. The absorbance is determined according to the Lambert-Beer law using pure water as a blank reference. When the LED chip emitting 275±10 nm deep-ultraviolet light works, the emitted light is detected by the photodiode C 13 to determine DOM concentration. When the LED chip emitting 230±10 nm deep-ultraviolet light works, the emitted light is detected by the photodiode C 13 to determine the nitrate concentration. As DOM also absorbs the 230±10 nm light, the absorbance for nitrate has to be corrected based on the organic matter's related absorbance at 275±10 nm. The correction formula is $A_{nitrate}=A_{230\pm10}-\alpha*A_{275\pm10}$, and α is determined to be 1.73, as shown in Table 1, through a spike-and-recovery assay. The LED emitting 465±10 nm blue light, the LED emitting 520±10 nm green light, and the LED emitting 655±10 nm red light are used to measure the absorption of blue light, green light and red light by the test water sample, respectively, via absorbance determination by the photodiode C 13, so as to determine water turbidity and also water color according to the primary color mixing principle and the relative absorption of each of the three visible lights.

The circuit board 8 of the electronic circuit unit comprises a microcontroller, a power supply module, LED driving circuits, signal amplification circuits, an analog-to-digital converter, a communication module, and a temperature sensor. The power supply module supplies power to components in the electronic circuit unit. The microcontroller outputs digital signals to the LED driving circuits to control the on/off of the LEDs emitting lights of different wavelengths in the composite LED module in a time-division multiplexing way, and to switch each LED on/off at a high switching rate of 1 kHz during its working period of 0.1 second. The three photodiodes A, B and C work in the photovoltaic mode, and the electronic signals generated in the three photodiodes are amplified by three signal amplification circuits (working as lock-in amplifiers) respectively. The signals of 1 kHz frequency from the LED chip having a high switching rate are processed by a phase sensitive detection module in the lock-in amplification circuits, output as DC signals and then go through a low pass filter, while the signals of the natural light are AC signals which are likely blocked by the low pass filter. The DC signals as obtained are converted in the analog-to-digital converter to digital signals and input to the microcontroller, wherein the microcontroller and the master computer use the MODBUS-RTU protocol for communication.

Figure 10:
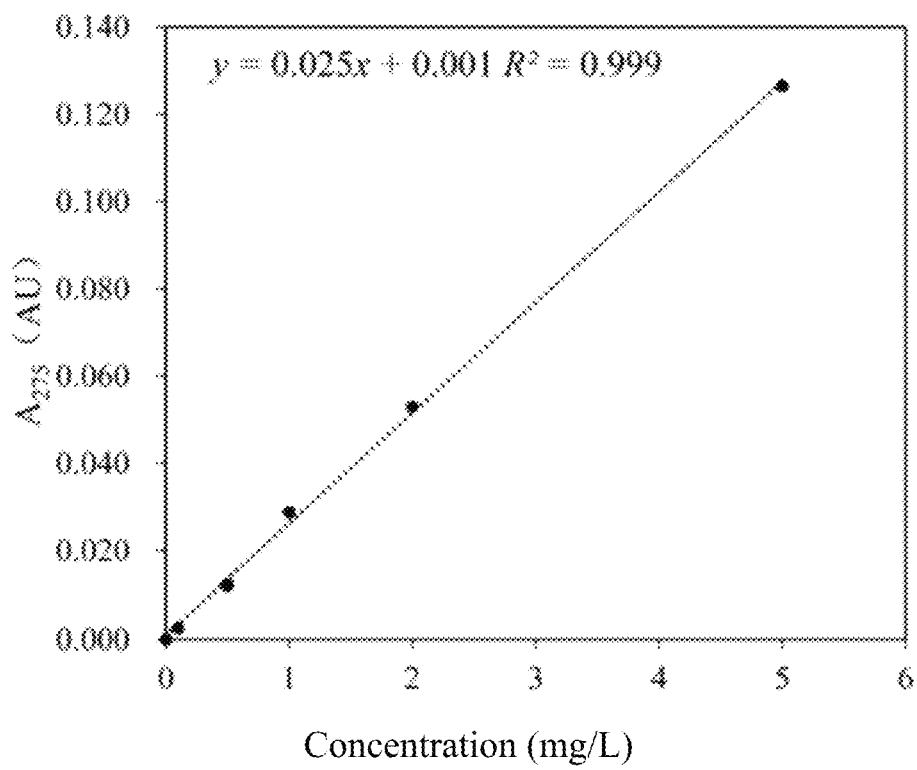
FIG. 10 shows a linear regression curve plotting a line that best fits the absorbance at 275 nm ($A_{275}$) over a range of a reference natural organic matter's concentration.

Solutions containing 0.0, 0.1, 0.5, 1.0, 2.0 and 5.0 mg/L Suwannee River natural organic matter (SR_NOM), a reference natural organic matter of International Humic Substances Society (IHSS), in water were prepared respectively, wherein the concentration of dissolved organic carbon was used as the SR_NOM concentration. The solutions were tested by the probe of the present Example. With the working of the LED emitting 275±10 nm deep-ultraviolet light, a linear regression curve was obtained plotting a line best fits the absorbance at 275 nm ($A_{275}$) over a range of SR_NOM concentration and shown in FIG. 10. The linear regression line equation was y=0.025x+0.001, with a $R^2$ as high as 0.999.

Figure 11:
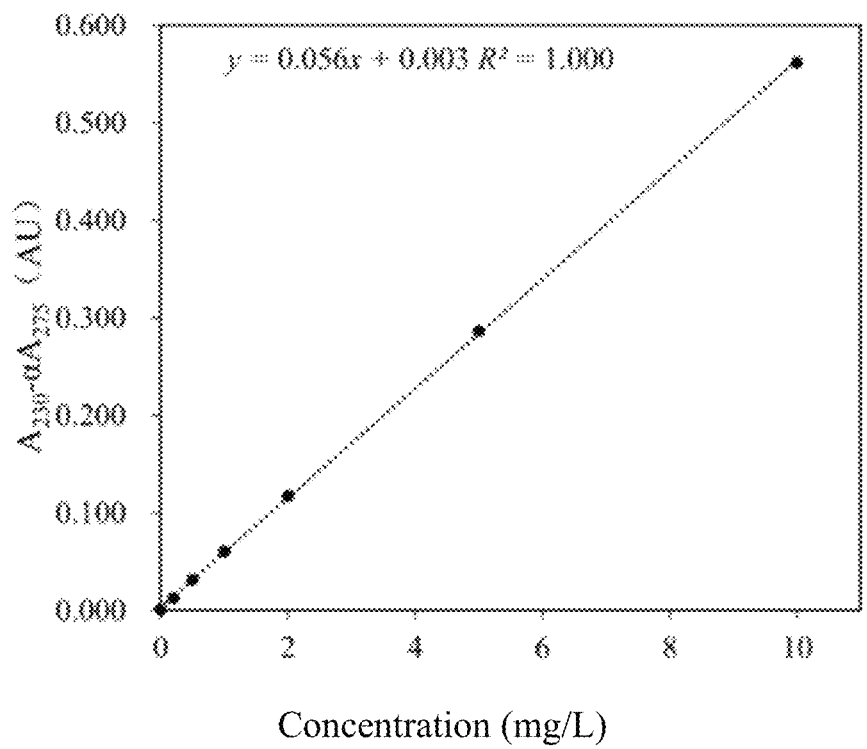
FIG. 11 shows a linear regression curve plotting a line that best fits the absorbance of the $NO_3^-$ containing solutions ($A_{230}$–1.73*$A_{275}$) over a range of $NO_3^-$ concentration.

The water solution containing 2.0 mg/L Suwannee River natural organic matter (SR_NOM), the reference natural organic matter of International Humic Substances Society (IHSS), was prepared. The SR_NOM containing solution and ultrapure water were added with $NO_3^-$ so that they contained 0.0, 0.2, 0.5, 1.0, 2.0, 5.0 and 10.0 mg/L nitrate nitrogen ($NO_3^-$—N), respectively. The solutions were tested by the probe of the present Example. Using the light from the LED emitting 275±10 nm deep-ultraviolet light and the light from the LED emitting 230±10 nm deep-ultraviolet light, the absorbance at 275 nm ($A_{275}$) and the absorbance at 230 nm ($A_{230}$) were obtained and listed in Table 1. The coefficient α was determined by assuming that the $A_{230}$ as measured on the ultrapure water made solution was equal to $A_{230}-\alpha*A_{275}$ as measured on the SR_NOM made solution containing the same $NO_3^-$, and the average, 1.73, was used as the final α. The correlation between the $A_{230}-1.73*A_{275}$ of the ultrapure water made solutions and the $NO_3^-$ concentration can be found in FIG. 11. The linear regression line equation was y=0.056x+0.003, with a $R^2$ as high as 1.000. Thus, the $NO_3^-$ concentration in a water sample can be determined using this linear regression curve.

TABLE 1

Absorbance of ultrapure water or SR_NOM-containing solutions containing $NO_3^-$ at different concentrations and coefficient α

| $NO_3^-$ concentration/ mg·L$^{-1}$ | $NO_3^-$ in ultrapure water | | $NO_3^-$ in 2 mg/l SR_NOM containing suspension | | |
|---|---|---|---|---|---|
| | $A_{230}$ | $A_{273}$ | $A_{230}$ | $A_{275}$ | α |
| 0.0 | −0.001 | −0.001 | 0.086 | 0.050 | 1.74 |
| 0.2 | 0.011 | −0.001 | 0.094 | 0.047 | 1.75 |
| 0.5 | 0.029 | −0.002 | 0.113 | 0.049 | 1.73 |
| 1.0 | 0.059 | −0.001 | 0.131 | 0.041 | 1.73 |
| 2.0 | 0.120 | 0.002 | 0.203 | 0.048 | 1.71 |
| 5.0 | 0.286 | 0.000 | 0.375 | 0.051 | 1.73 |
| Average | | | | | 1.73 |

Figure 12:
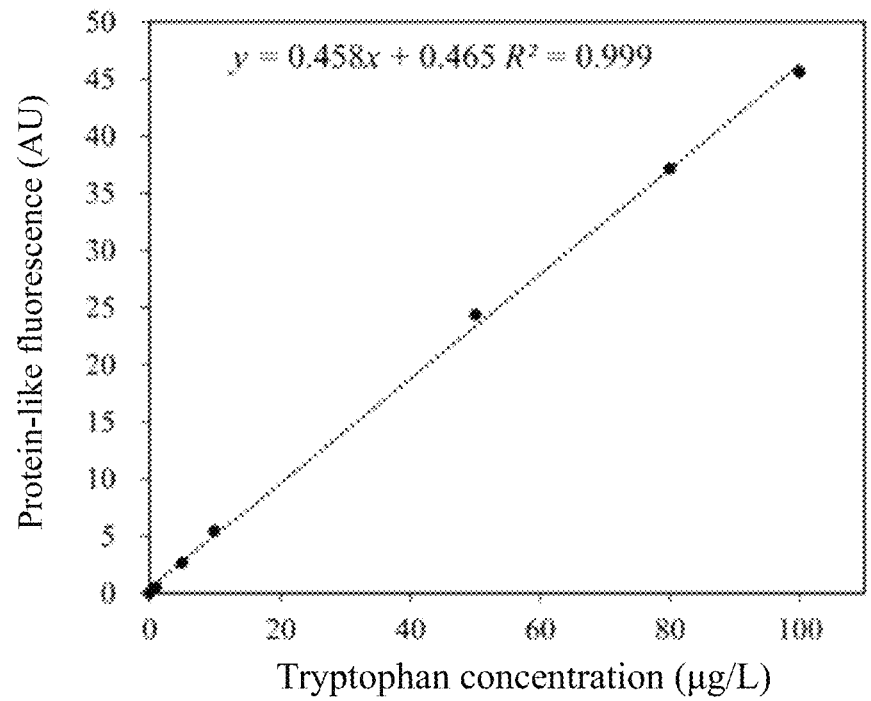
FIG. 12 is a linear regression curve plotting a line that best fits the protein-based fluorescence signal over a range of tryptophan concentration.
Figure 13:
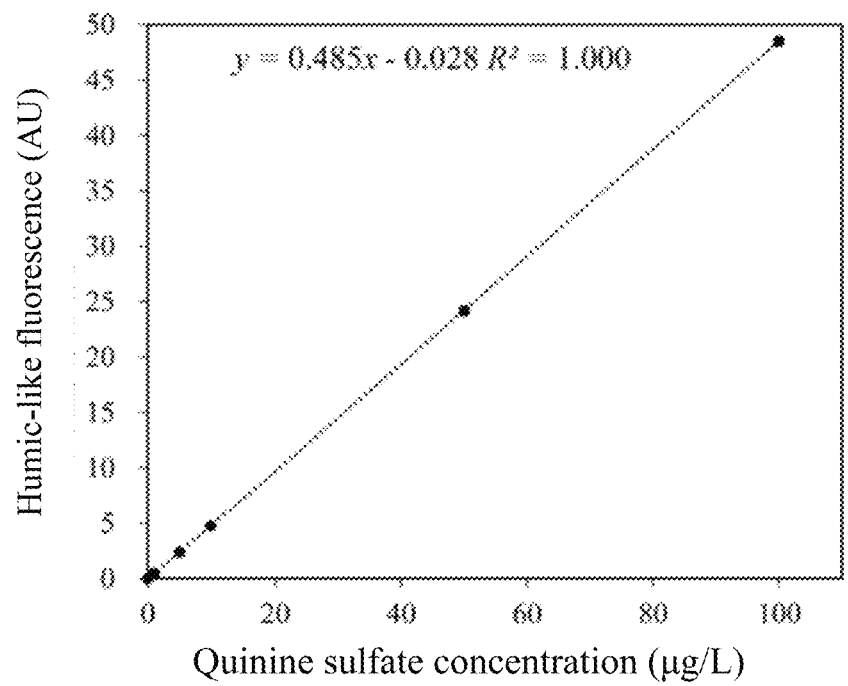
FIG. 13 is a linear regression curve plotting a line that best fits the humic-based fluorescence signal over a range of quinine sulfate concentration.

Water solutions containing tryptophan or quinine sulfate at different concentrations were prepared and tested using the probe of the present Example. When the LED emitting 275±10 nm deep-ultraviolet light was working, protein-based fluorescence and humic-based fluorescence was detected by the photodiode C 13. Linear regression curves were obtained with lines that best fit the fluorescence signal over a range of tryptophan and quinine sulfate concentration and shown in FIG. 12 and FIG. 13, respectively, both with a $R^2$ higher than 0.999, suggesting a high measurement accuracy.

Figure 14:
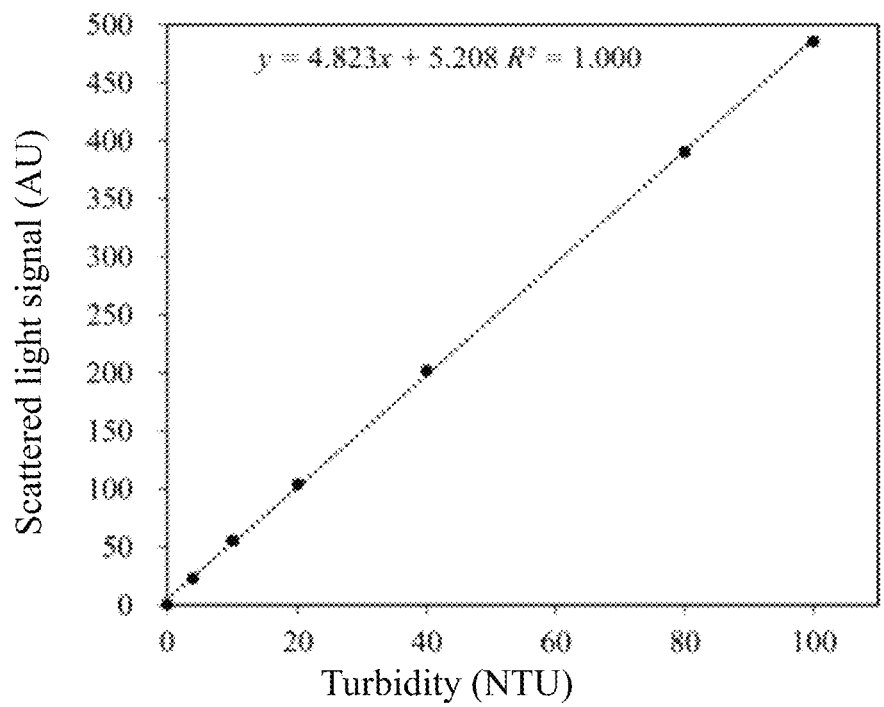
FIG. 14 is a linear regression curve plotting a line that best fits the scattered light signal over a range of turbidity.
Figure 15:
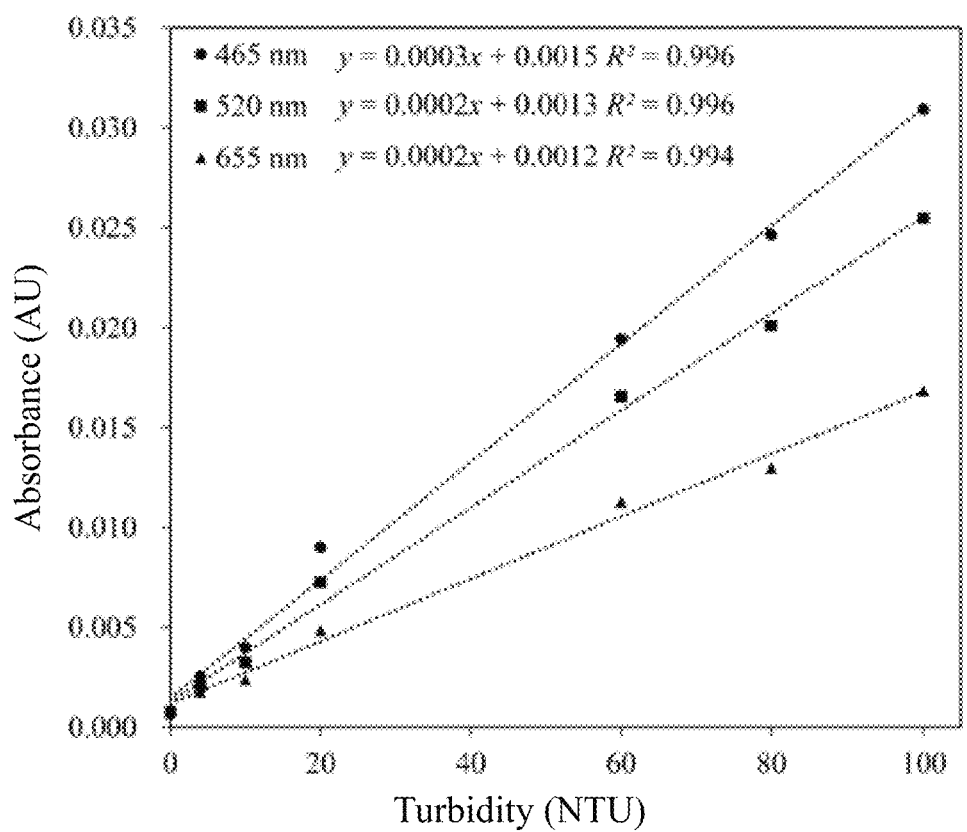
FIG. 15 shows linear regression curves plotting lines that best fit the absorbance $A_{465}$, $A_{520}$ and $A_{655}$ over a range of turbidity.

Water solutions containing hydrazine sulfate, a standard and reference matter for turbidity measurement, at different concentrations were prepared and tested using the probe of the present Example. Upon working of the LED emitting 465±10 nm blue light, a linear regression curve was obtained plotting a line that best fits the 465±10 nm scattered light over a range of turbidity. The curve was shown in FIG. 14 and had a linear regression equation y=4.823x+5.208 and a $R^2$ of 1.000. Further, linear regression curves plotting lines that best fit the absorbance $A_{465}$, $A_{520}$ and $A_{655}$ as measured when the LED chips emitting 465±10 nm blue light, 520±10 nm green light and 655±10 nm blue light worked over a range of turbidity were shown in FIG. 15, all lines with a $R^2$ higher than 0.99, suggesting the absorbance of the visible LED light beam and the turbidity are in linear correlation.

A water solution containing rose bengal, a dye, at a certain concentration was tested for the absorbance at 465±10 nm (Blue), 520±10 nm (Green) and 655 nm (Red), which were 0.025, 0.174 and 0.002 respectively. The data suggested that the solution did not absorb red light, absorb a lot of green light and had a weak blue light absorption, which was consistent with the complementary color theory that red and green are a complementary color pair in Newton's color wheel.

Example 2

The composite LED module based multi-parameter water quality monitoring probe in this Example differs from that in Example 1 in the following aspects.

Figure 6:
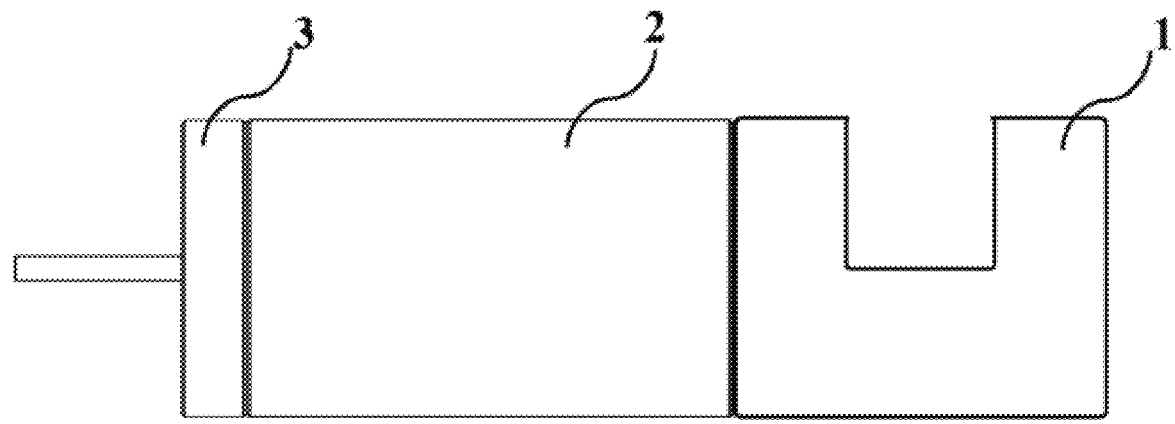
FIG. 6 is a schematic diagram showing the appearance of a multi-parameter water quality monitoring probe using a composite LED module according to a second embodiment.

As shown in FIG. 6, the casing contains a U-shaped front cover 1, a cylinder 2 and a back cover 3. The main body of the U-shaped front cover 1 is a cylinder, with a U-shaped groove on the side of the cylinder. The two lateral sides and the bottom part of the U-shaped groove are further provided with holes and a groove, and bonded with the JGS1 quartz plate A 5, quartz plate B 6 and quartz plate C 7 respectively, such that the U-shaped groove is waterproof and allows light transmission.

Figure 7:
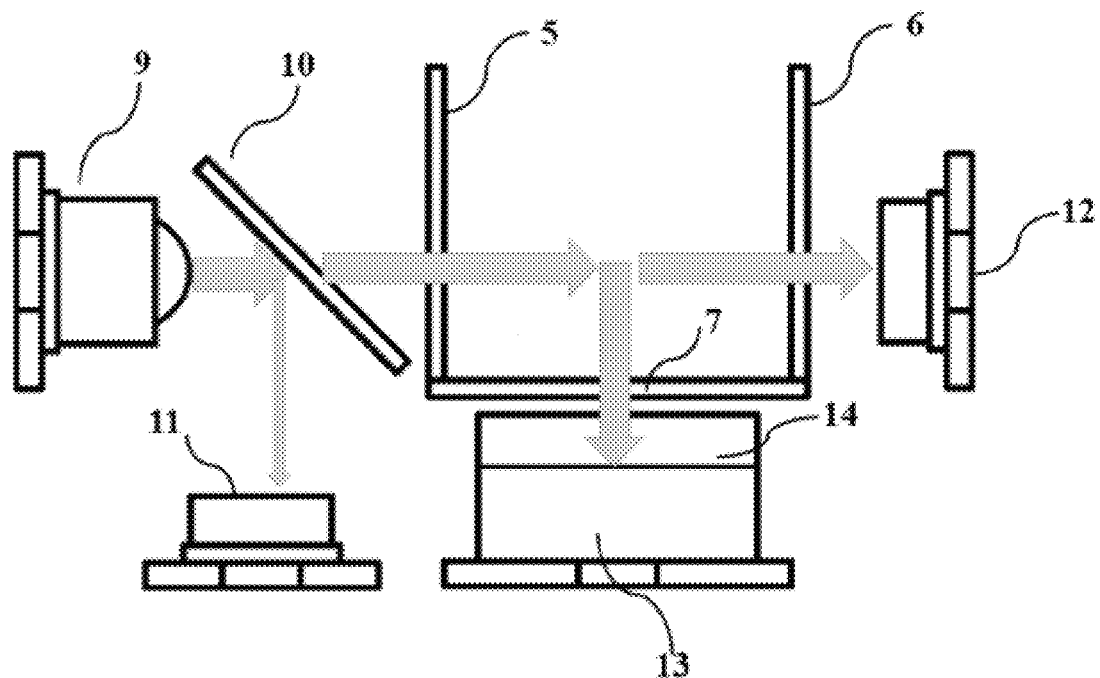
FIG. 7 is a schematic diagram showing an optical detection unit of the multi-parameter water quality monitoring probe using a composite LED module.

As shown in FIG. 7, the optical detection unit comprises the quartz plate A 5, the quartz plate B 6, the quartz plate C 7, a composite LED module 9, a beam splitter 10, a reference light-detecting photodiode A 11, an ultraviolet-visible light-detecting photodiode B 12, a fluorescence-detecting photodiode C 13, and a band-pass filter 14. The composite LED module 9 in this Example is arranged opposite to the quartz plate A 5. The light beam emitted from the LED module 9 is split into two beams by the beam splitter 10, wherein the light beam transmitting through the beam splitter is used for measurement, and the reflected light beam is used as a reference light. The optical power ratio of the light beam for measurement and the reference light beam is 90/10. The reference light-detecting photodiode A 11 and the ultraviolet-visible light-detecting photodiode B 12 are both UV-enhanced silicon photodiodes with TO-8 package. The ultraviolet-visible light-detecting diode B 12 is disposed to face the quartz plate B 6, so no reflector 15 is set in this Example.

Example 3

The composite LED module based multi-parameter water quality monitoring probe in this Example differs from that in Example 1 in the following aspects.

Figure 8:
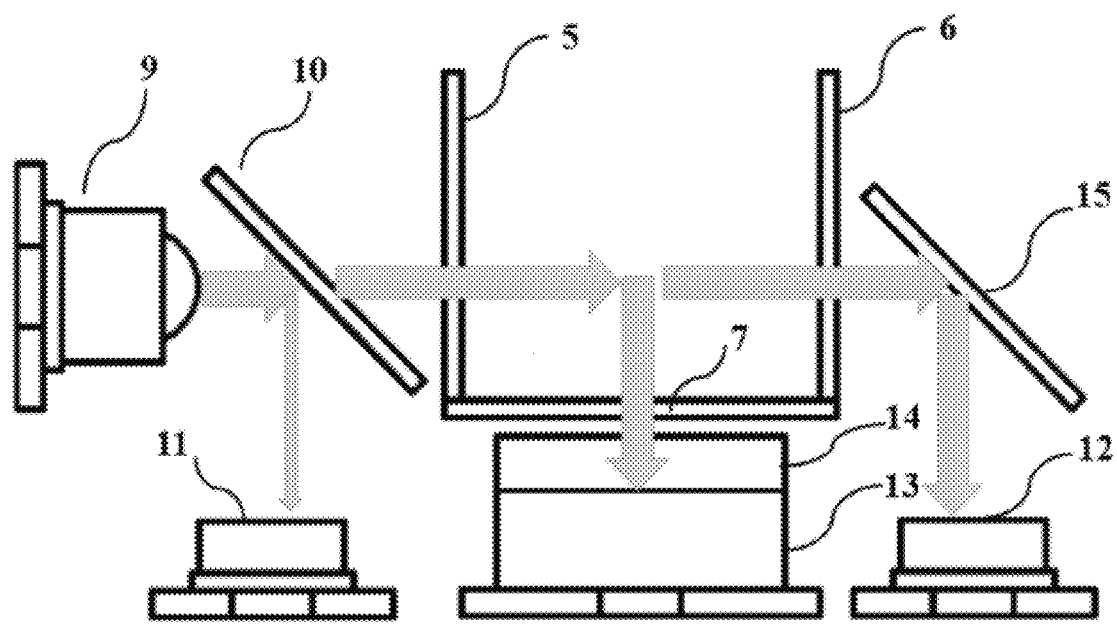
FIG. 8 is a schematic diagram showing an optical detection unit in a multi-parameter water quality monitoring probe using a composite LED module according to a third embodiment.

As shown in FIG. 8, the optical detection unit comprises a quartz plate A 5, a quartz plate B 6, a quartz plate C 7, a composite LED module 9, a beam splitter 10, a reference light-detecting photodiode A 11, an ultraviolet-visible light-detecting photodiode B 12, a fluorescence detecting photodiode C 13, a band-pass filter 14 and a reflector 15. In this Example, the composite LED module 9 is somewhat simplified and comprises a 230±10 nm deep-ultraviolet light LED, a 275±10 nm deep-ultraviolet light LED, and a 465±10 nm blue light LED packed together. The scattering or absorption of the blue light is mainly used for turbidity measurement. The composite LED module is arranged opposite to the quartz plate A 5. The light beam emitted from the LED module 9 is split into two beams by the beam splitter 10, wherein the light beam transmitting through the beam splitter is used for measurement, and the reflected light beam is used as a reference light. The optical power ratio of the light beam for measurement and the reference light beam is 90/10. The reference light detecting photodiode A 11 and the ultraviolet-visible light detecting photodiode B 12 are both UV-enhanced silicon photodiodes with TO-8 package.

Example 4

The composite LED module based multi-parameter water quality monitoring probe in this Example differs from that in Example 1 in the following aspects.

Figure 9:
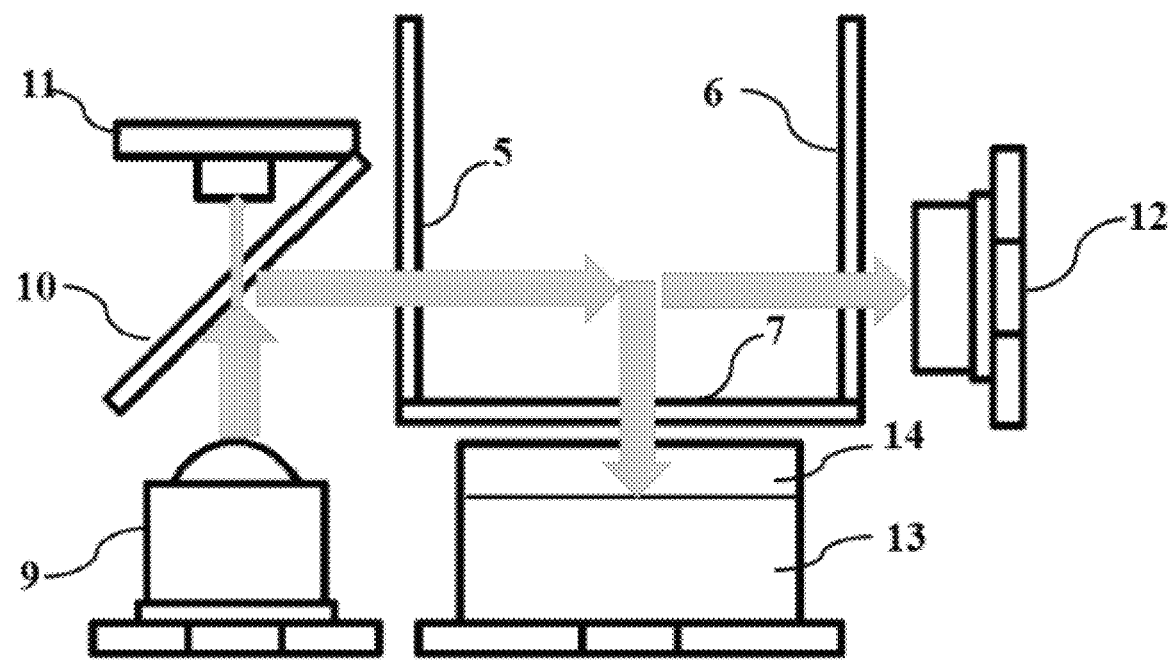
FIG. 9 is a schematic diagram showing an optical detection unit in a multi-parameter water quality monitoring probe using a composite LED module according to a fourth embodiment.

As shown in FIG. 9, the optical detection unit comprises a quartz plate A 5, a quartz plate B 6, a quartz plate C 7, a composite LED module 9, a beam splitter 10, a reference light-detecting photodiode A 11, an ultraviolet-visible light-detecting photodiode B 12, a fluorescence-detecting photodiode C 13, and a band-pass filter 14. In this Example, the composite LED module 9 is somewhat simplified and comprises a 230±10 nm deep-ultraviolet light LED, a 275±10 nm deep-ultraviolet light LED, and a 655±10 nm red light LED packed together. The red light is mainly used for turbidity measurement. The light beam emitted from the LED module 9 is split into two beams by the beam splitter 10, wherein the light beam transmitting through the beam splitter is used as a reference light, and the reflected light is used for measurement. The optical power ratio of the reference light beam to the light beam for measurement is 20/80. The reference light-detecting photodiode A 11 and the ultraviolet-visible light-detecting photodiode B 12 are both UV-enhanced silicon photodiodes with TO-8 package. The ultraviolet-visible light detecting diode B 12 is disposed to face the quartz plate B 6, so no reflector 15 is set in this Example.

Example 5

The composite LED module based multi-parameter water quality monitoring probe in this Example differs from that in Example 1 in the following aspects.

The composite LED module 9 is somewhat simplified and comprises a 230±10 nm deep-ultraviolet light LED and a 275±10 nm deep-ultraviolet light LED packed together. A TO-46 package is used to pack the ultraviolet-visible light-detecting photodiode B 12, and the fluorescence-detecting photodiode C 13 is a silicon photovoltaic plate with TO-46 package.

We claim:

1. A multi-parameter water quality monitoring device, comprising:
   a composite LED module, wherein the composite LED module comprises:

a 230±10 nm deep-ultraviolet light LED,
a 275±10 nm deep-ultraviolet light LED, and
0 to 3 visible light LED(s), wherein these LEDs are packaged on a substrate or circuited board and configured in such a way that each LED is switched on/off independently,
a U-shaped groove in which a water sample flows,
an ultraviolet-visible light detecting photodiode B,
a fluorescence detecting photodiode C, and
a band-pass filter.

2. The multi-parameter water quality monitoring device according to claim 1, wherein the U-shaped groove comprises a quartz plate A, a quartz plate B, and a quartz plate C, wherein the quartz plate A and the quartz plate B are arranged opposite each other, and the quartz plate C is horizontally arranged on the bottom of the U-shaped groove and perpendicular to the quartz plate A and quartz plate B.

3. The multi-parameter water quality monitoring device according to claim 2, wherein the light beam emitted from the composite LED module transmits to the water sample in the U-shaped groove where light absorption, scattering and fluorescence emission occur, wherein the emitted fluorescence goes across the quartz plate C and the band-pass filter and is detected by the fluorescence-detecting photodiode C, while the blue light scattered by particulates and/or colloids passes through the band-pass filter for humic-based fluorescence detection and detected by the fluorescence-detecting photodiode C, and the light that has not been absorbed and scattered by water sample goes across the quartz plate B and reaches the ultraviolet-visible light detecting photodiode B.

4. The multi-parameter water quality monitoring device according to claim 1, further comprising
a beam splitter, and
a reference light detecting photodiode A.

5. The multi-parameter water quality monitoring device according to claim 4, wherein the beam splitter is arranged at a 45° angle relative to the central axis of the composite LED module.

6. The multi-parameter water quality monitoring device according to claim 4, wherein the beam splitter splits a light beam from the composite LED module into two beams at an optical power ratio ranging from 10/90 to 90/10.

7. The multi-parameter water quality monitoring device according to claim 4, wherein the central axis of the composite LED module is arranged perpendicular to the central axis of the U-shaped groove, and the central axis of the reference light detecting photodiode A is arranged perpendicular to that of the composite LED module.

8. The multi-parameter water quality monitoring device according to claim 4, wherein the central axis of the composite LED module is arranged in parallel to the central axis of the U-shaped groove, and the central axis of the reference light-detecting photodiode A is arranged in parallel to that of the composite LED module.

9. The multi-parameter water quality monitoring device according to claim 3, further comprising a reflector for reflecting a light to the ultraviolet-visible light-detecting photodiode B.

10. The multi-parameter water quality monitoring device according to claim 1, wherein the reference light detecting photodiode A and the ultraviolet-visible light detecting photodiode B are UV enhanced silicon photodiodes or composite photodiodes each packaged with an AlGaN based deep-ultraviolet light detecting chip and a silicon photovoltaic plate.

11. The multi-parameter water quality monitoring device according to claim 10, wherein the silicon photovoltaic plate is 凹-shaped and the AlGaN based deep-ultraviolet light-detecting chip is in the groove part of the 凹-shaped silicon photovoltaic plate.

12. The multi-parameter water quality monitoring device according to claim 1, wherein the band-pass filter is (a) a band-pass filter covering 320-360 nm for detection of protein-based fluorescence, (b) a band-pass filter covering 380-500 nm for detection of humic-based fluorescence, or (c) a band-pass filter covering 320-500 nm for detection of the total fluorescence from both proteins and humic substances.

13. A multi-parameter water quality monitoring probe, comprising
a casing,
an optical detection unit, and
an electronic circuit unit, wherein the optical detection unit comprises the multi-parameter water quality monitoring device according to claim 1.

14. The multi-parameter water quality monitoring probe according to claim 13, wherein the casing comprises
a U-shaped front cover, configured to receive and fix the optical detection unit,
a cylinder, configured to receive the electronic circuit unit,
a back cover, configured to fix a power cable in a water-tight way.

15. The multi-parameter water quality monitoring probe according to claim 13, wherein the electronic circuit unit comprises a microcontroller, a power supply module, a signal amplification circuit, an analog-to-digital converter, a communication module, and a temperature sensor.

* * * * *